US008637695B2

(12) United States Patent
Lewis et al.

(10) Patent No.: US 8,637,695 B2
(45) Date of Patent: *Jan. 28, 2014

(54) SYNTHESIS OF ORGANOHALOSILANE MONOMERS FROM CONVENTIONALLY UNCLEAVABLE DIRECT PROCESS RESIDUE

(75) Inventors: Kenrick Martin Lewis, Flushing, NY (US); John David Neely, Clifton Park, NY (US)

(73) Assignee: Momentive Performance Materials Inc., Albany, NY (US)

(*) Notice: Subject to any disclaimer, the term of this patent is extended or adjusted under 35 U.S.C. 154(b) by 120 days.

This patent is subject to a terminal disclaimer.

(21) Appl. No.: 13/340,882

(22) Filed: Dec. 30, 2011

(65) Prior Publication Data
US 2013/0172593 A1  Jul. 4, 2013

(51) Int. Cl.
C07F 7/14 (2006.01)

(52) U.S. Cl.
USPC ........................................................ 556/468

(58) Field of Classification Search
USPC .................................................. 556/467, 468
See application file for complete search history.

(56) References Cited

U.S. PATENT DOCUMENTS

| | | | |
|---|---|---|---|
| 2,598,435 | A | 5/1952 | Mohler et al. |
| 2,681,355 | A | 6/1954 | Barry et al. |
| 2,709,176 | A | 5/1955 | Bluestein |
| 2,787,627 | A | 4/1957 | Kuriyagawa et al. |
| 2,842,580 | A | 7/1958 | Gilbert et al. |
| 3,432,537 | A | 3/1969 | Guinet et al. |
| 3,639,105 | A | 2/1972 | Atwell et al. |
| 4,059,608 | A | 11/1977 | Calas et al. |
| 4,070,071 | A | 1/1978 | Caravito |
| 4,298,559 | A | 11/1981 | Baney et al. |
| 4,393,229 | A | 7/1983 | Ritzer et al. |
| 4,552,973 | A | 11/1985 | Feldner et al. |
| 4,888,435 | A | 12/1989 | Chadwick et al. |
| 5,292,909 | A | 3/1994 | Chadwick et al. |
| 5,292,912 | A | 3/1994 | Chadwick et al. |
| 5,326,896 | A | 7/1994 | Chadwick et al. |
| 5,416,232 | A | 5/1995 | Brendler et al. |
| 5,502,230 | A * | 3/1996 | Mautner et al. ............... 556/468 |
| 5,627,298 | A | 5/1997 | Freeburne et al. |
| 2005/0113592 | A1 | 5/2005 | Wagner et al. |

FOREIGN PATENT DOCUMENTS

| | | |
|---|---|---|
| DE | 3208829 | 12/1982 |
| DE | 3410644 | 9/1985 |
| DE | 3436381 | 4/1986 |
| DE | 4207299 | 11/1993 |
| EP | 0861844 | 2/1998 |
| EP | 1533315 | 5/2005 |
| FR | 2427302 | 12/1979 |
| WO | WO2011008009 | 1/2011 |

OTHER PUBLICATIONS

Lewis, Kenrick M., "Selective Hydrogenolysis of Methylchlorodisilanes Using Rhenium-Containing Catalysts", ACS National Meeting, San Francisco (Apr. 1992) Abstract.
Taketa, Akira et al., "Hydrocracking of Disilanes", Chemical Abstracts, vol. 53, col. 17888i (1957).
Shiina, Kyo et al., "Cleavage of Organosubstituted Disilanes and Sisilmethylenes by Hydrogen Chloride", Chemical Abstracts, vol. 53, col. 17889b (1957).
Matsumoto, Hideyuki et al., "Conversion of Disilanes to Functional Monosilanes", Bulletin of the Chemical Society of Japan, vol. 51, No. 6, pp. 1913-1914 (1978).
Urenovitch, Joseph V. et al., "The Condensation-Polymerization of Pentamethyldisilanyl Cyanide and Related Compounds", Journal of American Chemical Society, vol. 83, pp. 3372-3375 (1963).
Urenovitch, Joseph V. et al., "Formation of Higher Silanes by the Tetramethylammonium Chloride-Catalyzed Disporportionation of Methylchlorodisilanes", Journal of the Chemical Society, pp. 5563-5564 (1963).
Matsumoto, Hideyuki et al., "A Convenient and Large Scale Synthesis of 1,1,2-Trimethyl-1,2,2-Trichlorodisilane and 1,1,2,2-Tetramethyl-1,2-Dichlorodisilane", Journal of Organometallic Chemistry, vol. 142, pp. 149-153 (1977).
Sakurai, Hideki et al., "Aluminum Chloride-Catalyzed Reactions of Organosilicon Compounds II", Tetrahedron Letters, No. 45, pp. 5493-5497 (1966).
Ishikawa, Mitsuo et al., "Preparation of Some Polysilicon Halides by Aluminum Halide Catalyzed Interchange of Methyl and Halogen on Silicon", Journal of Organometallic Chemistry, vol. 23, pp. 63-69 (1970).
Zhang, Ning et al., "Conversion of a Direct Process High-Boiling Residue to Monosilanes by a Two-Step Catalysis Approach", Res. Chem. Intermed., vol. 33, No. 7, pp. 613-622 (2007).
Garcia-Escomel, Cristina et al., "Catalytic Cleavage of the Si-Si Bond of Methylchlorodisilanes with Nucleophiles: Evidences for a Stablised Silylene Reaction Intermediate", Inorganica Chimica Acta, vol. 350, pp. 407-413 (2003).
Calas, R. et al., "Scission, Par Des Composes A Liaison", Journal of Organometallic Chemistry, vol. 74, pp. 371-376 (1974) Abstract in English.
Trandell, Roger F. et al., "A Study of the Amine-Induced Disporportionations of Various Methylchlorodisilanes", Journal of Inorganic Nuclear Chemistry, vol. 40, pp. 1305-1308 (1978).
Baney, Ronald H. et al., "Methylchloropolysilanes and Derivatives Prepared from the Redistribution of Methylchlorodisilanes", Organometallics, vol. 2, No. 7, pp. 859-864 (1983).
Herzog, U. et al., "Methylchlorooligosilanes as Products of the Basecatalysed Disporportionation of Various Methylchlorodisilanes", Journal of Organometallic Chemistry, vol. 507, pp. 221-228 (1996).
Perrin, D. D., "Dissociation Constants of Organic Bases in Aqueous Solution", Austrailian National University, Canberra, pp. 5-7 (1965).
Earle, Martyn J. et al., "Ionic Liquids. Green Solvents for the Future", Pure Applied Chemistry, vol. 72, No. 7, pp. 1391-1398 (2000).
Del Sesto, Rico E. et al., "Tetraalkylphosphonium-Based Ionic Liquids", Journal of Organometallic Chemistry, vol. 690, pp. 2536-2542 (2005).
Hawkins, L. G., "Gas Chromatographic Analysis of Methylchlorosilanes Produced by the Direct Reaction", Catalyzed Direct Reactions of Silicon, K. M. Lewis and D. G. Rethwisch, Editors, Elsevier Science Publishers, pp. 189-205 (1993).

* cited by examiner

*Primary Examiner* — Samantha Shterengarts
*Assistant Examiner* — Amanda L Aguirre
(74) *Attorney, Agent, or Firm* — Dominick G. Vicari; Joseph S. Ostroff; Wiggin and Dana LLP

(57) ABSTRACT

Disclosed herein is a catalytic process for the synthesis of organohalosilane monomers from tetraorganodihalodisilanes and other compounds that are not cleaved during the conventional hydrochlorination of Direct Process Residue. The process is characterized by the use of a catalyst containing (1) one or more heterocyclic amines and/or one or more heterocyclic ammonium halides, and (2) one or more quaternary Group 15 onium compounds.

28 Claims, No Drawings

SYNTHESIS OF ORGANOHALOSILANE MONOMERS FROM CONVENTIONALLY UNCLEAVABLE DIRECT PROCESS RESIDUE

CROSS REFERENCE TO RELATED APPLICATIONS

U.S. patent application Ser. No. 13/341,157 filed on even date herewith and entitled SYNTHESIS OF ORGANOHALOSILANE MONOMERS VIA ENHANCED CLEAVAGE OF DIRECT PROCESS RESIDUE is incorporated herein by reference in its entirety.

FIELD OF THE INVENTION

The present invention relates to the synthesis of organohalosilane monomers from the high-boiling by-products formed from the Direct Synthesis of alkylhalosilanes and arylhalosilanes. In particular, this invention discloses the synthesis of $(CH_3)_2SiHCl$, $CH_3SiHCl_2$ and $(CH_3)_2SiCl_2$ from $Cl(CH_3)_2SiSi(CH_3)_2Cl$ and other compounds that are not cleaved during the conventional hydrochlorination of Direct Process Residue.

BACKGROUND OF THE INVENTION

Alkylhalosilanes and arylhalosilanes are valuable precursors to silicones and organofunctional silanes that are used in a broad range of industries. Methylchlorosilanes and phenylchlorosilanes are particularly valuable and are the most commonly manufactured products of these classes. The primary commercial method to prepare alkylhalosilanes and arylhalosilanes is through the Rochow-Müller Direct Process (also called Direct Synthesis and Direct Reaction), in which copper-activated silicon is reacted with the corresponding organohalide in a gas-solid or slurry-phase reactor. Gaseous products and unreacted organohalide, along with fine particulates, are continuously removed from the reactor. Hot effluent exiting from the reactor comprises a mixture of copper, metal halides, silicon, silicides, carbon, gaseous organohalide, organohalosilanes, organohalodisilanes, carbosilanes and hydrocarbons. Typically this mixture is first subjected to gas-solid separation in cyclones and filters. Then the gaseous mixture and ultrafine solids are condensed in a settler or slurry tank from which the organohalide, organohalosilanes, hydrocarbons and a portion of organohalodisilanes and carbosilanes are evaporated and sent to fractional distillation to recover the organohalosilane monomers. Organohalodisilanes and carbosilanes left in the post-distillation residues are typically fed to secondary treatment such as hydrochlorination. The solids accumulated in the settler along with the less volatile silicon-containing compounds are purged periodically and sent to waste disposal or to secondary treatment.

Organohalodisilanes, organohalopolysilanes and carbosilanes, related siloxanes and hydrocarbons, either in the post-distillation residues or in the slurry purged from the reactor, boil above organohalosilane monomers. Collectively they are referred to as Direct Process Residue (DPR). The terms, higher boilers, high-boiling residue and disilane fraction, are also used interchangeably with DPR. DPR can account for 1 to 10 weight percent of the Direct Synthesis product mixture and, owing to the considerable accompanying tonnage, about 1 to 8 percent of the total raw material cost of the Rochow-Müller Process. In current commercial practice, the DPR is sent to hydrochlorination in which some components of DPR are reacted with HCl in the presence of a tertiary amine catalyst, such as tri(n-butyl)amine, to provide organohalosilane monomers. However, some components of DPR are unreactive in the process and are discharged to waste treatment. Commercial methylchlorosilane plants dispose of thousands of tons of slurry and hydrochlorination waste per year at considerable cost and loss of raw material values. There are also environmental impacts of the waster disposal methods employed.

There have been many disclosures about recovering organohalosilane monomers and other values from DPR through cleavage, redistribution and disproportionation processes.

Cleavage is the term used to describe the process whereby disilanes, trisilanes, polysilanes and carbosilanes are reacted to produce monomeric silanes. Hydrochlorination and hydrogenolysis are examples of cleavage processes. Redistribution is the rearrangement of groups bonded to silicon atoms such that new molecules are produced during the reaction. For example, in the equation shown below, the compounds of the class $R^1{}_2SiX_2$ are formed by redistribution of $R^1{}_3SiX$ and $R^1SiX_3$. The reverse reaction, whereby $R^1{}_2SiX_2$ is converted to the original reactants is called disproportionation.

$$R^1{}_3SiX + R^1SiX_3 \leftrightarrows 2R^1{}_2SiX_2 \tag{1}$$

Illustratively, in the case of the secondary treatment of the DPR from the Direct Synthesis of methylchlorosilanes, the literature have disclosed the following: catalytic hydrochlorination as is disclosed in U.S. Pat. No. 2,598,435; U.S. Pat. No. 2,681,355; U.S. Pat. No. 2,709,176; U.S. Pat. No. 2,842,580; U.S. Pat. No. 3,432,537; U.S. Pat. No. 5,627,298 and EP 861844; and by H. Matsumoto, et al in *Bulletin Chemical Society Japan*, vol 51 (1978) 1913-1914; catalytic hydrochlorination with immobilized tertiary amine catalysts as disclosed in DE 4,207,299; thermal hydrochlorination as is disclosed in EP 1533315 and U.S. Pat. No. 5,292,912; and by K. Shiina, et al. in *Chemical Abstracts*, vol 53 (1957) 17889b; catalytic hydrogenolysis as is disclosed in U.S. Pat. No. 2,787,627; U.S. Pat. No. 3,639,105; U.S. Pat. No. 4,070,071; U.S. Pat. No. 4,059,608; U.S. Pat. No. 5,292,909; U.S. Pat. No. 5,326,896 as well as in K. M Lewis, 203rd ACS National Meeting, San Francisco, April 1992, Abstract INOR 52; and A. Taketa, et al., *Chemical Abstracts*, vol 53 (1957) 17888i; catalytic redistribution/disproportionation with Lewis Acids as is disclosed in U.S. Pat. No. 4,393,229; U.S. Pat. No. 4,552,973; U.S. Pat. No. 4,888,435 as well as in J. Urenovitch, et al, *J. Amer. Chem. Soc.*, vol 83 (1963) 3372-3375, ibid. 5563-5564; H. Matsumoto, et al., *J. Organometallic Chemistry*, vol 142 (1977) pp 149-153; Sakurai, et al., *Tetrahedron Letters*, #45 (1966) 5493-5497; and Ishikawa, et al., *J. Organometallic Chemistry*, vol 23 (1970) 63-69; Lewis Acid catalyzed catalytic redistribution of Direct Process Residue with methylchlorosilane monomers, including the lower boiling fraction (boiling point<43° C.) from the Direct Process, as has been disclosed in U.S. Pat. No. 4,393,229; DE 3,208,829; DE 3,436,381; DE 3,410,644; US 2005/0113592 A1 and by Zhang, et al., *Res. Chem. Intermed.*, vol 33 (2007) pp 613-622; catalytic redistribution/disproportionation with Lewis Bases as is disclosed in U.S. Pat. No. 4,298,559; U.S. Pat. No. 5,416,232; Fr. Pat. 2,427,302 as well as in R. Trandwell, et al., *J. Inorg. Nucl. Chem.*, vol 40 (1978) 1405-1410; C. Garcia-Escomel, et al., *Inorg. Chim. Acta.*, vol 350 (2003) 407-413 and R. Calas, et al., *J. Organometallic Chemistry*, vol 71 (1974) 371-376.

While the cited prior art processes may afford recovery of methylchlorosilane monomers and some are practiced commercially, the ability of these processes to convert highly methylated chlorodisilanes, such as $(CH_3)_3SiSi(CH_3)_2Cl$ and $Cl(CH_3)_2SiSi(CH_3)_2Cl$, or carbosilanes such as $Cl_2CH_3Si—CH_2—Si(CH_3)_2Cl$ to organohalosilane monomers remains to be less than satisfactory. Illustratively, Trandell et al., *J. Inorg. Nucl. Chem.*, 40 (1978) 1305-1308) reported that $Cl(CH_3)_2SiSi(CH_3)_2Cl$ did not disproportionate in the presence of trimethylamine even when heated to 65° C. for four months and 100° C. or two months. Garcia-Escomel, et al., (*Inorg. Chim, Acta*, Vol 350 (2003) 407-413) state that $Cl(CH_3)_2SiSi(CH_3)_2Cl$ was unreactive when treated with a variety of phosphines, phosphites, phosphine oxides and tetraalkylammonium halide Lewis bases at 140-150° C. According to Baney, et al., (*Organometallics*, 2 (1983) 859-864) $Cl(CH_3)_2SiSi(CH_3)_2Cl$ remains unreacted when heated with tetrabutyl phosphonium chloride up to 150° C. Herzog, et al. (*J. Organometallic Chem.* 507 (1996) 221-229) employed higher, unspecified temperatures and N-methylimidazole as catalyst and observed the formation of a white solid, characterized as $(CH_3)_2SiCl_2$ complexed with two molecules of the catalyst, and tri- and tetra-silanes.

Recently, there are disclosures that are said to produce monomeric silanes from highly methylated chlorodisilanes. For example, JP A 54-9228 discloses the hydrochlorination of $Cl(CH_3)_2SiSi(CH_3)_2Cl$ with $[(C_6H_5)_3P]_4Pd$ as catalyst to produce $(CH_3)_2SiHCl$. For the same purpose, U.S. Pat. No. 5,502,230 discloses the use of a catalyst composition consisting of Pd(0) or Pt(0) and an additive chosen from a tertiary amine, carboxylic amide, alkylurea, tertiary phosphine, phosphoric amide, quaternary ammonium halide or quaternary phosphonium halide. U.S. Pat. No. 7,655,812 discloses a method of preparing $(CH_3)_2SiHCl$ via hydrochlorination of $Cl(CH_3)_2SiSi(CH_3)_2Cl$ comprising the use of Pd(0), a tertiary amine and a tertiary phosphine in which at least one of the hydrocarbyl groups is a functionalized aryl group. However, all these processes require the use of expensive noble metals in the catalyst compositions thus making them too expensive to be commercially practicable.

Furthermore, even for conventionally cleavable DPR, the monomers produced by the prior art processes tend to contain more $CH_3SiCl_3$ monomer than otherwise would be desirable. It is generally agreed that the organohalosilane monomers of general formula $R^1SiX_3$ are less valuable than those of general formula, $R^1_2SiX_2$, $R^1_3SiX$, $R^1SiHX_2$ and $R^1_2SiHX$. In the case of methylchlorosilanes, the compounds can be ranked in value based on selling prices of commercial quantities or of smaller amounts for laboratory research. Using prices published on the internet or in specialty chemical catalogs, such as Gelest, Inc., the value ranking of the methylchloro-silane monomers is $(CH_3)_2SiHCl>CH_3SiHCl_2>(CH_3)_3SiCl>(CH_3)_2SiCl_2>CH_3SiCl_3$. Unfortunately, the monomer mixture produced by this commercial process is enriched in less valuable $CH_3SiCl_3$ relative to other more valuable monomers and the gravimetric ratio, $(CH_3SiCl_3/(CH_3)_2SiCl_2)$, is typically greater than 1.0.

Accordingly, an objective of the present invention is the provision of a process for preparing organohalosilane monomers from conventionally uncleavable Direct Process Residue which does not involve the use of expensive noble catalysts, which provides reduced $R^1SiX_3$ and increased $R^1_2SiHX$, $R^1SiHX_2$ and $R^1_2SiX_2$ compared to conventional commercial processes such as tertiary amine catalyzed hydrochlorination, and which is easily conducted at moderate temperatures and relatively short reaction times.

SUMMARY OF THE INVENTION

In one aspect, the present invention relates to a catalytic process for producing an organohalosilane monomer composition from a high-boiling residue. The process includes the steps of:

(A) heating the high-boiling residue in the presence of a catalyst comprising (1) one or more heterocyclic amines and/or one or more heterocyclic ammonium halides, and (2) one or more quaternary Group 15 onium compounds, optionally in the presence of an organohalide and/or a hydrogen halide and/or an inert gas, at a temperature within the range of about 75° C. to about 300° C. under atmospheric pressure or superatmospheric pressure to convert the high-boiling residue to an organohalosilane monomer composition containing at least one organohalosilane monomer having a general formula selected from the group consisting of $R^1SiHX_2$, $R^1_2SiHX$, $R^1_2SiX_2$ and $R^1_3SiX$, $R^1$ being an aromatic, aliphatic, alkaryl or cycloaliphatic univalent hydrocarbyl group, X being a halogen atom selected from the group consisting of fluorine, chlorine, bromine, and iodine, and (B) optionally recovering the catalyst, wherein the high-boiling residue comprises (1) an uncleavable component containing at least one of tetraorganodihalodisilanes and optionally one or more compounds selected from carbosilanes, organohalopolysilanes, hexaorganodisilanes, and pentaorganohalodisilanes; and (2) optionally a cleavable component containing at least one of diorganotetrahalodisilanes and triorganotrihalodisilanes with the proviso that if present, the cleavable component has a concentration less than that of the uncleavable component; and wherein the quaternary Group 15 onium compound is of the general formula, $R_4Q^+X^-$, wherein each R is independently an alkyl, cycloalkyl, aryl or alkaryl group of from 1 to 30 carbon atoms, Q is phosphorus, arsenic, antimony and bismuth, and X is a halide selected from the group consisting of F, Cl, Br or I.

The process of the invention is effective in converting conventionally uncleavable compounds such as $Cl(CH_3)_2SiSi(CH_3)_2Cl$ to valuable monomers like $(CH_3)_2SiHCl$, $CH_3SiHCl_2$ and $(CH_3)_2SiCl_2$ by using readily available catalysts at moderate temperatures and relatively short reaction times.

DETAILED DESCRIPTION OF THE INVENTION

The present invention provides a catalytic process for converting a high-boiling residue into organohalosilane monomers of the general formulae $R^1SiX_2$, $R^1_2SiHX$, $R^1_3SiX$ and $R^1SiX_3$, particularly $R^1SiHX_2$, $R^1_2SiHX$ and $R^1_2SiX_2$. As used herein, $R^1$ is an aromatic, aliphatic, alkaryl or cycloaliphatic univalent hydrocarbyl group and X is a halogen atom such as fluorine, chlorine, bromine or iodine. Examples of $R^1$ are methyl, ethyl, phenyl, cyclohexyl, allyl, vinyl and benzyl. Advantageously, $R^1$ is methyl, ethyl or phenyl and X is chloride or bromide. More advantageously, $R^1$ is methyl and X is chloride. In one embodiment, the catalytic process of the invention provides an organohalosilane monomer composition containing $(CH_3)_2SiHCl$, $CH_3SiHCl_2$, $(CH_3)_3SiCl$, $(CH_3)_2SiCl_2$, and $CH_3SiCl_3$, wherein the content of $(CH_3)_2SiCl_2$ and $CH_3SiHCl_2$, individually or collectively, exceeds that of $CH_3SiCl_3$.

Suitable high-boiling residues contain an uncleavable component and optionally a cleavable component with the proviso that if present, the cleavable component has a concentration less than that of the uncleavable component.

As used herein, organohalodisilanes, organohalopolysilanes, and carbosilanes that are not converted to monomeric silanes by tertiary amine-catalyzed hydrochlorination are termed "uncleavable" or "conventionally uncleavable."

Those that can be converted to monomeric silanes are called "cleavable" or "conventionally cleavable."

The uncleavable component suitable for the present invention contains at least one of tetraorganodihalodisilanes and optionally at least one of carbosilanes, organohalopolysilanes, hexaorganodisilanes, and pentaorganohalodisilanes.

Tetraorganodihalodisilanes are represented by the general formula of $XR^1_2SiSiR^1_2X$, wherein $R^1$ and $X$ have the same meanings as defined herein above for organohalosilane monomers. Examples of tetraorganodihalodisilanes include $Cl(CH_3)_2SiSi(CH_3)_2Cl$ and $Br(CH_3)_2SiSi(CH_3)_2Br$.

Hexaorganodisilanes and pentaorganohalodisilanes are represented by the general formulae of $R^1_3SiSiR^1_3$ and $XR^1_2SiSiR^1_3$ respectively, wherein $R^1$ and $X$ have the same meanings as defined herein above for organohalosilane monomers. Examples include $(CH_3)_3SiSi(CH_3)_3$ and $Cl(CH_3)_2SiSi(CH_3)_3$.

Carbosilanes have one or more methylene (—CH$_2$—) groups and can be represented by the general formula, $R^1_hX_jSi$—$(CH_2)_w$—$SiX_kR^1_l$, wherein h, j, k and l are individually 0 provided that h+j=3 and k+l=3, w≥1, preferably 1-4, and $R^1$ and $X$ have the same meanings as defined herein above for organohalosilane monomers. Examples of carbosilanes include compounds having the general formulae $R^1X_2Si$—$CH_2$—$SiXR^1_2$ and $R^1X_2Si$—$CH_2$—$CH_2$—$SiX_2R^1$ with $R^1$=$CH_3$ and X=Cl. Carbosilanes with a single —CH$_2$— group between the silicon atoms are also called silylmethylenes or disilamethanes.

Organohalopolysilanes are those of the formula $R^1_mX_qSi$—$(Si(R^1X)_n$—$SiX_qR^1_m$ wherein the subscripts m and q are individually 0 with the sum of m+q=3, n is an integer greater than 2, $R^1$ and $X$ have the same meanings as defined herein above for organohalosilane monomers.

The cleavable component in the high-boiling residue contains at least one of diorganotetrahalodisilanes and triorganotrihalodisilanes. Suitable diorganotetrahalodisilanes are represented by the formulae: $X_2R^1SiSiR^1X_2$ and $XR^1_2SiSiX_3$. Suitable triorganotrihalodisilanes are represented by the formulae: $X_2R^1SiSiR^1_2X$ and $R^1_3SiSiX_3$. $R^1$ and $X$ have the same meanings as defined herein above for organohalosilane monomers. Exemplary diorganotetrahalodisilanes and triorganotrihalodisilanes include $Cl_2(CH_3)SiSi(CH_3)Cl_2$, $Cl(CH_3)_2SiSiCl_3$, $(CH_3)_3SiSiCl_3$, and $Cl_2(CH_3)SiSi(CH_3)_2Cl$.

In one embodiment, the high-boiling residue according to the invention is the uncleavable residue from the conventional hydrochlorination of DPR. In addition to the disilanes, $(CH_3)_3SiSi(CH_3)_3$, $Cl(CH_3)_2SiSi(CH_3)_3$ and $Cl(CH_3)_2SiSi(CH_3)_2Cl$, this high-boiling residue comprises trisilanes, carbosilanes and the tertiary amine/tertiary amine hydrochloride catalyst used to effect the hydrochlorination. The methylchlorosilane monomer composition obtained from the cleavage of this conventionally uncleavable feedstock is enriched in $(CH_3)_2SiHCl$, $CH_3SiHCl_2$, $(CH_3)_3SiCl$ and $(CH_3)_2SiCl_2$ as compared to $CH_3SiCl_3$.

In the present process, the high-boiling liquid residue, as described above, is heated in the presence of a catalyst containing (1) one or more heterocyclic amines, and/or one or more heterocyclic ammonium halides, and (2) one or more quaternary Group 15 onium compounds of general formula, $R_4Q^+X^-$, wherein each R is independently an alkyl, cyclo alkyl, aryl or alkaryl group of from 1 to 30 carbon atoms, Q is a Group 15 element such as phosphorus, arsenic, antimony and bismuth, and X is a halide atom such as F, Cl, Br or I. It is appreciated that the R groups are not necessarily all the same. The catalyst can be formed external to the reactor and later added to the reactor, or internal to the reactor by adding the individual components of the catalyst to the reactor directly. Similarly, the catalyst and the high-boiling residue can be combined outside the reactor or they may be added to it individually.

Conversion of the high-boiling residue into organohalosilane monomers comprises chemical reactions such as redistribution/disproportionation of disilanes, carbosilanes and monomeric silanes as well as cleavage of disilanes, polysilanes and carbosilanes. Hence the present invention is also directed to the catalytic disproportionation and redistribution of $R^1$, X and H groups on carbosilanes and disilanes as is illustrated by the following equations:

(2)

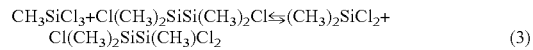

(3)

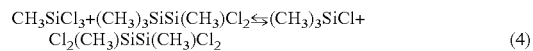

(4)

It should be understood that while the above equations might represent overall changes, there can be separate intermediate elementary steps involved in these transformations. For example, equation (3) can involve the separate steps shown in equations (5) and (6). Similarly, equation (4) might comprise the steps shown in equations (7) and (8).

Decomposition of the disilane $(Cl(CH_3)_2SiSi(CH_3)_2Cl)$ to monomer $((CH_3)_2SiCl_2)$ and silylene $((CH_3)_2Si)$

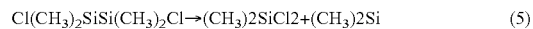

(5)

Insertion of the silylene $((CH_3)_2Si)$ into a monomer $(CH_3SiCl_3)$ with formation of a new disilane $(Cl(CH_3)_2SiSi(CH_3)Cl_2)$

(6)

Decomposition of the disilane $((CH_3)_3SiSi(CH_3)Cl_2)$ to monomer $((CH_3)_3SiCl)$ and silylene $(CH_3SiCl)$

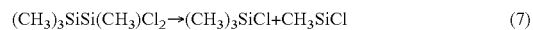

(7)

Insertion of the silylene $(CH_3SiCl)$ into a monomer $(CH_3SiCl_3)$ with formation of a new disilane $(Cl_2(CH_3)SiSi(CH_3)Cl_2)$

(8)

When combined, the heterocyclic amines, and/or heterocyclic ammonium halides, and the quaternary Group 15 onium compounds exhibit polarity, basicity and nucleophilicity sufficient to effect the cleavage, redistribution and disproportionation of the disilanes, carbosilanes, trisilanes and other polysilanes in the high-boiling residue and the redistribution and disproportionation of the initially formed monomeric silanes, so as to produce a desirably valuable monomer composition.

According to the instant invention, the heterocyclic amine component of the catalyst comprises a heterocyclic hydrocarbon having at least one nitrogen atom in at least one hydrocarbon ring, in which the positioning of the nitrogen ensures that the molecule exhibits polarity, basicity and nucleophilicity sufficient to effect the desired catalysis. The heterocyclic amines of the invention have at least one nitrogen atom in at least one 4- to 8-membered hydrocarbon ring, where the ring atoms adjacent to the nitrogen can be carbon or nitrogen and the hydrocarbon ring or rings are, independently of one another, aromatic or non-aromatic hydrocarbon rings.

The nitrogen in the hydrocarbon ring can also be bonded to H or to branched or linear alkyl groups, advantageously C1 to C6-alkyl; or to oxygen, halogen, trialkoxysilyl, or $NR'_2$, in which R' is H, linear or branched C1 to C6 alkyl, or trialkoxysilyl or two sigma and one pi bond in the ring, or the bridgehead to a further ring.

Depending on the bonding to the adjacent ring atoms, the carbon in the hydrocarbon ring can be mono- or disubstituted by H, linear or branched alkyl, advantageously C1 to C6 alkyl, halogen, oxygen, or $NR'_2$, in which R' is H, linear or branched C1 to C6 alkyl, or trialkoxysilyl or carry a further hydrocarbon ring system or it forms the bridgehead to a further ring system. The substituents can, independently of one another, be identical or different.

Nitrogen-containing heterocyclic hydrocarbons which are particularly suitable for the catalyst of the present invention are, for example, 5-membered rings having from 1 to 3 nitrogen atoms in the hydrocarbon ring, preferably imidazole, 1-methylimidazole, 2-methylimidazole, 2-ethylimidazole, 2-isopropyl-imidazole, 4-methylimidazole, 2,4-dimethylimidazole, 2-(2-imidazolyl)imidazole, 2-phenylimidazole, imidazoline, imidazolidine, pyrazole, 3-methylpyrazole, pyrrolidone, N-methylpyrrolidone, 1,3-dimethyl-2-imidazolidone or 1,2,3-triazole, 1,2,4-triazole or 6-membered rings having at least one nitrogen atom in the hydrocarbon ring, preferably 2,2'-bipyridine, 1,3-dimethyl-3,4,5,6-tetrahydro-2(1H)pyrimidone or N,N-dibutylpiperazine or polycyclic hydrocarbons having at least one nitrogen atom in the hydrocarbon ring, preferably benzimidazole, benzotriazole, Urotropin, 1,5,7-triazabicyclo[4.4.0]dec-5-ene, 1,8-diazabicyclo-[5.4.0]undec-7-ene, 1,5-diazabicyclo[4.3.0]non-5-ene, diazabicyclo-octane. 2-Methylimidazole and 4-methylimidazole are preferred components for the catalyst of the present invention. Also preferred are heterocyclic amines with pKa 6.9-7.9. pKa values of the amines are published in a variety of sources, including *Dissociation Constants of Organic Bases in Aqueous Solution* by D. D. Perrin, relevant portions of which are incorporated herein by reference. The pKa values of some specific heterocyclic amines are indicated in parentheses following the names: imidazole (pKa 6.95), 2-methylimidazole (pKa 7.85), and 4-methylimidazole (pKa 7.52). Commercial supplies of heterocyclic amines may contain a low percentage of impurities. For example, 2-methylimidazole may contain about 0.05 to about 5 weight percent of imidazole.

Nitrogen atoms in heterocyclic amines are trivalent. When one or more nitrogen atoms is quaternized (that is, tetravalent and positively charged), the compound is a heterocyclic ammonium compound. Thus, imidazoles become imidazolium compounds when the nitrogen atoms at positions 1 and 3 are quaternized. Examples are imidazole hydrochloride, 1-butyl-3-methylimidazolium chloride, 1-(3-cyanopropyl)-3-methylimidazolium chloride, 1-methylimidazolium chloride and 1-octyl-3-hexylimidazolium bromide. Heterocyclic ammonium halides, such as the imidazolium halides, can be formed in situ during the practice of the instant invention in the case wherein hydrogen halide, for example, HCl or HBr, is present in the high-boiling residue. Alternatively, the heterocyclic ammonium halides can be generated intentionally via addition of gaseous hydrogen halides and organohalides to the heterocyclic amine. The addition can be in a separate synthetic preparation, or it can be done in situ in the catalytic reactor with the heterocyclic amine, optionally admixed with the quaternary Group 15 onium compound and/or the high-boiling liquid residue.

Ionic liquids refer to organic salts that are liquid at temperatures less than 100° C. See M J. Earle, et al., in *Pure & Applied Chem.*, vol. 72 (2000) pp 1391-1398, which is fully incorporated herein by reference. Heterocyclic ammonium halides that are liquid at temperatures less than 100° C. fall within the definition of ionic liquids. Examples are 1,2-dimethyl-3-(n-propyl)-imidazolium chloride, 1-ethyl-3-methylimidazolium bromide, 1,2-dimethyl-3-(n-butyl) imidazolium chloride, 1-butyl-3-methyl-imidazolium chloride, 1-(3-cyanopropyl)-3-methyl-imidazolium chloride, and 1-methylimidazolium chloride. In one embodiment, the heterocyclic ammonium halide is an ionic liquid selected from the group consisting of 1-methylimidazolium chloride, 1-butyl-3-methylimidazolium chloride, and 1-(3-cyanopropyl)-3-methylimidazolium chloride.

Examples of quaternary Group 15 onium compounds are tetra(n-butyl)phosphonium chloride, tetra(n-butyl)phosphonium bromide, trihexyl(tetradecyl)phosphonium bromide, methyltri(isobutyl)phosphonium bromide, methyltri(isobutyl)phosphonium chloride, tetra(n-octyl)phosphonium chloride, tri(n-butyl)tetradecylphosphonium chloride, and octyltri(butyl)phosphonium chloride. Tetra(n-butyl)phosphonium chloride is a preferred component for the catalyst of the present invention.

Quaternary Group 15 onium compounds and mixtures thereof, which are liquid at temperatures below 100° C. fall within the definition of ionic liquids as defined by R. Sesto, et al., in *J. Organometallic Chem.*, vol. 690 (2005) pp 2836-2842, which is fully incorporated herein by reference. Examples of these ionic liquids are tri(hexyl)tetradecylphosphonium chloride (CYPHOS® IL 101), tetra(n-butyl)phosphonium bromide (CYPHOS® IL 163), tetra(n-butyl)phosphonium chloride (CYPHOS® IL 164), tri(n-butyl) tetradecylphosphonium chloride (CYPHOS® IL 167) and methyltri(isobutyl)phosphonium chloride. In one embodiment, the instant catalytic process comprises use of quaternary Group 15 onium ionic liquids for the recovery of organohalosilane monomers from the high-boiling residue.

Commercial supplies of the quaternary Group 15 onium compounds are likely to contain low percentage amounts of the compounds of general formulae $R_3QHX$, and HX, in which R, Q and X have the same meanings as defined above in the context of quaternary Group 15 onium compounds. For example, tetra(n-butyl)phosphonium chloride, $(n-C_4H_9)_4PCl$, can contain about 0.05 to about 5 weight percent, specifically about 0.1 to about 1.0 weight percent of HCl and about 0.05 to about 5 weight percent, specifically about 0.1 to about 1.0 weight percent of $(n-C_4H_9)_3PHCl$.

Advantageously, the catalysts of the invention, which contain (1) heterocyclic amines and/or heterocyclic ammonium halides, and (2) quaternary Group 15 onium compounds, are liquid at temperatures less than 100° C. In general, they have low vapor pressures in the temperature range specified herein for converting the high-boiling residue to the organohalosilane monomer composition. If the individual components of the catalysts are liquid at temperatures less than 100° C., then they can be added together and mixed to prepare the desired compositions. If, however, one or more is solid, then, advantageously, the component melting below 100° C. is heated to obtain a liquid and the other(s) are later dissolved in it. Catalysts, which are liquid below 100° C., are illustrated in the examples below. Melting behavior of the catalysts of the invention can be investigated by visual observations of the catalysts during heating and cooling cycles as well as by differential scanning calorimetry (DSC) and similar techniques.

Catalytic cleavage, redistribution and disproportionation of the compounds in the high-boiling residue can be realized with the combinations of (1) heterocyclic amines and/or heterocyclic ammonium halides, and (2) quaternary Group 15 onium compounds having a wide range of gravimetric and molar values. In one embodiment, the catalyst contains from about 0.01 weight percent to about 99.95 weight percent of (1) heterocyclic amines and/or heterocyclic ammonium halides and from about 0.05 weight percent to 99.9 weight percent of (2) quaternary Group 15 onium compounds based on the total weight of components (1) and (2). In one embodiment, the catalyst of the invention contains 5 wt % to 85 wt % of 2-methylimidazole and 95 wt % to 15 wt % of tetra(n-butyl)-phosphonium chloride based on the total weight of the 2-methylimidazole and the tetra(n-butyl)-phosphonium chloride. Advantageously, the weight ratio of the heterocyclic amines and/or the heterocyclic ammonium halides relative to the quaternary Group 15 onium compounds is from about 1:9 to about 9:1, more advantageously from about 1:3 to about 3:1. On a molar basis, in certain embodiments, it is desirable to have a molar excess of heterocyclic amines and/or heterocyclic ammonium halides relative to quaternary Group 15 onium compounds. Thus, in the case of tetra(n-butyl)phosphonium chloride and 2-methylmidazole, the molar ratio of the imidazole to the phosphonium chloride can be from 1.1 to 100, specifically 1.5 to 60 and more specifically 1.5 to 20.

The present process requires the presence of a "catalytic amount" of a catalyst as described above. By the term "catalytic amount" it is meant an amount of catalyst sufficient to facilitate the conversion of the high-boiling residue to monomeric organohalosilanes. A preferred catalytic amount is the amount that is sufficient to facilitate the conversion of the high-boiling residue to an organohalosilane monomer composition that is rich in compounds of general formula, $R^1SiHX_2$, $R^1_2SiHX$, $R^1_2SiX_2$, and $R^1_3SiX$ and deficient in the compounds of the general formula $R^1SiX_3$ such that the gravimetric ratio of $R^1SiX_3$ to $R^1_2SiX_2$ is less than that obtained when the high-boiling residue is similarly heated in the absence of any catalyst, or is subjected to a tertiary-amine catalyzed hydrochlorination, and is preferably less than 1.0; and the gravimetric ratio of $(R^1SiHX_2+R^1_2SiHX+R^1_2SiX_2+R^1_3SiX)/R^1SiX_3$ is greater than 2. The optimum amount of the catalyst required will depend upon the catalysts used and the compositions of the high-boiling residue. Such amounts can be determined experimentally by those skilled in the art. In the case of treating the high-boiling residue from the Direct Synthesis of methylchlorosilane, methylbromosilane, ethylchlorosilane or phenylchlorosilane, the total weight of the catalyst of the invention is 1 to 50 weight percent based on the weight of high-boiling residue charged to the reactor for batchwise operation. Advantageously, it is 5 to 25 weight percent and, more advantageously, 8 to 20 weight percent. When recovery and reuse of the catalyst is practiced, multiple batches of high-boiling residue can be converted on a single catalyst charge. In this mode of operation, the ultimate catalyst usage, defined as 100×(weight of the catalyst/total weight of the high-boiling residue, can be as low as 5 weight percent, advantageously 1 weight percent, more advantageously as low as 0.1 weight percent.

Catalytic cleavage, redistribution and disproportionation of the compounds in the high-boiling residue is carried out in reactors that can be operated safely at high pressures and temperatures and that also have means for agitation of the reaction mixture. The reactors should also be suitable for contact with corrosive materials such as halosilanes and organohalosilanes. The process may be run in a batch or continuous mode. In one embodiment, the catalyst and the high-boiling residue are added first to the reactor. Optionally, organohalide (for example, methyl chloride) and/or hydrogen halide (for example, HCl or HBr, advantageously HCl) and/or an inert gas (for example nitrogen or argon) is added until a predetermined pressure reading has been stably established. The predetermined pressure is advantageously less than or equal to the value indicative of saturation at the ambient temperature. The quantity of HCl to be charged is 0.1-10 grams per 100 grams of the high-boiling residue. Preferably, it is 0.3-1.5 grams per 100 grams of the high-boiling residue feed.

Next, the reactor is heated from ambient temperature to between about 75° C. and about 500° C., advantageously to between about 75° C. and about 300° C., more advantageously to between about 100° C. and about 280° C., to effect the catalysis leading to the formation of the organohalosilane monomer composition. The set temperature is maintained for periods of 1 to 600 minutes, specifically greater than about fifteen minutes up to about 4 hours to convert the high-boiling residue to the desired monomer composition. A preferred time is 30 minutes up to about 2 hours. When heating is discontinued, the reactor and its contents are allowed to cool to room temperature, or some other convenient value, to permit safe and efficient separation and recovery of the organohalosilane monomers from the reaction mixture. The retentate, which contains the catalysts and the compounds with normal boiling points higher than those of the organohalosilane monomers, is recharged with high-boiling residue and the process is repeated. This reuse and recycle of the original catalyst charge can be repeated many times.

In another embodiment, the process of the instant invention can be conducted at atmospheric pressure. When the process is operated at atmospheric pressure, organohalosilane monomers produced by the cleavage and redistribution/disproportionation reactions will be discharged from the reactor at temperatures at which they have significant vapor pressure. Typically, the reaction mixture is agitated and heated to from about 140 to about 250° C., advantageously from about 140 to about 180° C. Organohalide (for example, methyl chloride) and/or hydrogen halide (for example, HCl) is optionally injected for a brief period or for the entire duration of the experiment. Monomeric methylchlorosilanes have been observed to begin to distill over when the reactor temperature is in the range of from about 130° C. to about 150° C. Reactions at atmospheric pressure are continued until the organohalosilane monomers no longer distill over. Thereafter, the reactor is cooled to a temperature at which fresh high-boiling residue can be recharged safely and the catalysis is repeated with the retained catalyst.

As discussed above, the catalytic process of the invention can be conducted at atmospheric pressure or superatmospheric pressure. In one embodiment, superatmospheric pressures are generated autogenously when the reactor is closed during the process. The ultimate pressures attained depend on the molar quantity of reagents and products and the reaction temperature and can be up to 7 MPa. Under the closed conditions, the organohalosilanes can undergo further redistribution and disproportionation reactions. Accordingly, the product composition obtained under atmospheric pressure can be different from that produced autogenously. In particular, lower amounts of the compounds of formula, $R^1_2SiHX$ are obtained and more of $R^1_2SiX_2$ and $R^1SiHX_2$ under autogenous conditions.

When the operating pressure is atmospheric and reaction products are volatilized from the reactor, the vapors can be fractionated in one or more distillation columns for isolation of pure organohalosilane monomers. In another process variant, the vapors are condensed and the liquid recovered for subsequent fractional distillation. When the reactor is closed during the process, it can be cooled to allow the temperature and pressure to decrease to values that permit safe, quantitative recovery of the reaction products. Thus, the reactor may be cooled to room temperature or lower so that any residual pressure can be released safely and liquid reaction products can be recovered for distillation. Alternatively, the reactor can be vented to a fractionating column or condenser while the reactor is still hot and its contents are vaporous.

The catalyst can be recovered as a solid or liquid residue after volatilization of the reaction mixture. Additional starting materials can be added to this residue for another catalytic cycle. Multiple catalytic cycles are thereby possible. Overall, many batches of high-boiling residue can be treated with a single charge of catalyst. Thus, effective catalyst usage is less than ten weight percent and preferably 0.1 to about 5 weight percent based on weight of catalyst charged in the first cycle divided by the total weight of the feedstock charged in all the cycles.

The reactions are conducted batchwise or continuously in ionic liquids in a mechanically-stirred reactor, a gas-sparged reactor or a bubble column. In one embodiment, the process of this invention is conducted continuously by injecting the high-boiling residue into the bottom of a heated reaction column containing the catalyst in liquid form, preferably an ionic liquid. The reaction column is maintained at about 100 to about 300° C. where the liquid catalyst is stable and components in the high-boiling residue can be converted to organohalosilane monomers. Advantageously, the high-boiling residue is heated, even to a vapor, prior to injection into the reaction column. The reaction column can be topped with a reflux column to separate the more volatile organohalosilane monomers from unreacted and/or higher boiling compounds in the reactor effluent.

The following examples are intended to illustrate, but in no way limit the scope of the present invention. All parts and percentages are by weight and all temperatures are in degrees Celsius unless explicitly stated otherwise.

EXAMPLES

In the examples, Me represents the methyl radical, $CH_3$, and Bu is butyl, $C_4H_9$.

Gas Chromatography (GC) was done on an HP5890 chromatograph with thermal conductivity detection. The column used for the analysis of the methylchlorosilane monomers was 30.48 cm×0.64 cm (12 ft×0.25 inch) stainless steel packed with 30 weight percent OV-210 on Chromosorb P AWDMCS 80/100 mesh. Separation conditions were those disclosed by L. G. Hawkins in *Catalyzed Direct Reactions of Silicon*, K M Lewis and D. G. Rethwisch, Editors, Elsevier Science Publishers, 1993, pp 189-205, which is fully incorporated herein by reference. A 30.48 cm×0.32 cm (12 ft×0.125 inch) stainless steel column packed with 20 weight percent OV-101 on Chromosorb WHP was used for the analysis of carbosilanes, disilanes and polysilanes.

Gas Chromatography/Mass Spectrometry (GC/MS) analyses were carried out with an Agilent 6890GC/5973 MSD instrument fitted with a 30 meter-long ZB5 (5% phenyl, 95% methylpolysiloxane) capillary column. Column inner diameter was 0.25 mm and film thickness was 2.5 µm. The carrier gas was helium with 200:1 injection split ratio. The injection port and GC/MS interface temperatures were 250° C. and 270° C., respectively. Injection volume was 1 µl. The oven temperature was held at 50° C. for 2 minutes before it was raised at a rate of 8° C./min to 340° C., and then was held for 16 minutes. The mass spectrometer was operated in the EI (70 eV electron impact ionization) full scan (m/z 10-800) mode.

DSC (Differential Scanning calorimetry) measurements were made with a TA Instruments DSC Q100 calorimeter.

For NMR characterization, samples were analyzed with a Bruker AVANCE 600 Spectrometer operating at field strength of 14.1T. Protons ($^1H$'s) resonate at 600 MHz at this field strength. Samples for $^{29}Si$ NMR were prepared as a 25% to 30% by volume solution in $Cr(AcAc)_3/CDCl_3$ to a final Cr salt concentration of ~0.05M $Cr(AcAc)_3$. The solution was placed in a 10 mm NMR tube. Chemical shifts were externally referenced to tetramethylsilane (TMS). An inverse gated decoupling pulse sequence was used with a pulse width of 45-degrees for $^{29}Si$. A delay of 10 s was used between scans (AQ of 1.4 s). The data were processed using a LB of 2 Hz.

TABLE 1

| MATERIALS USED IN ILLUSTRATIVE EXAMPLES | |
|---|---|
| NAME | SUPPLIER |
| 2-Methylimidazole, 99% purity | Aldrich |
| 2-Methylimidazole, 99% purity | BASF |
| 2-Methylimidazole, 98.5% purity (contains 1.5% imidazole) | BASF |
| 4-Methylimidazole, 98% purity | Aldrich |
| 1-Methylimidazole, 98% purity | Aldrich |
| 1,2,4-Triazole, 98% purity | Aldrich |
| Tetra(n-butyl)phosphonium Chloride 96% purity | Aldrich |
| 1-Methylimidazolium Chloride | Aldrich |
| 1-Butyl-3-Methylimidazolium Chloride | Aldrich |
| 1-(3-cyanopropyl)-3-methylimidazolium Chloride | Aldrich |
| CYPHOS ® 443 (Tetra (n-butyl)phosphonium chloride, 96%) | Cytec |
| CYPHOS ® IL 167 (aka CYPHOS ® 3453), Tri(n-butyl)tetradecylphosphonium chloride | Cytec |
| CYPHOS ® IL 101 (Tri n-hexyl)tetradecyl-phosphonium chloride | Cytec |
| 1,2-Dichloro-1,1,2,2-tetramethyldisilane | Gelest |
| Direct Process Residues | Momentive |

Example 1A-1B

This Example illustrates the preparation of methylchlorosilane monomers from a Direct Process Residue sample containing more than 50 wt % of the conventionally uncleavable methylchlorodisilanes, $(CH_3)_3SiSi(CH_3)_3$, $Cl(CH_3)_2SiSi(C_3)_3$ and $Cl(CH_3)_2SiSi(CH_3)_2Cl$. The experiment of Example 1A was run autogenously in a 300 ml autoclave at 175° C. for 1 hour, while that of Example 1B was done in laboratory glassware at atmospheric pressure at the temperature and time indicated herein below.

Example 1A

The 300 ml autoclave was cleaned, dried and purged with nitrogen. It was then charged with 5 g $(n-C_4H_9)_4PCl$ (96% purity, Aldrich), 5 g 2-Methylimidazole (99% purity, Aldrich) and 100 g disilane feedstock having the composition shown in Table 2. After its closure, the autoclave was pressurized with $CH_3Cl$ to obtain a stable reading of 137.88 kPa (20 psig) at 20° C. The stirrer was set at 150 rpm; and the autoclave was heated to 175° C. and maintained at that temperature for 1 hour. The maximum pressure attained was 1.08 MPa (157 psig). The heating mantle was then removed; and the reactor was allowed to cool to room temperature. The residual pressure, 262 kPa (38 psig) at 20° C. was discharged slowly. Then the reactor was opened to retrieve the reaction mixture. 105.3 g liquid and 10.6 g solid were obtained.

GC analysis of the liquid portion of the reaction product is summarized in Table 2.

Example 1B

This experiment was conducted in a 250 ml 4-necked round bottom flask with 104 g the same disilane feedstock used in Example 1A, 5 g (n-C$_4$H$_9$)$_4$PCl (CYPHOS® 443) and 5 g 2-Methylimidazole (98.5% purity, BASF). The flask was fitted with a heating mantle, short distillation column, stirrer, N$_2$ inlet and thermocouple. The distal end of the column was connected to a dry-ice/isopropanol condenser, which was attached to a receiving flask. A second thermocouple was positioned at the head of the column. It was set at 72° C. and used to control the heating mantle. Heat was applied to the stirred contents of the flask. Product began coming over after ~55 minutes when the pot temperature was 105° C. and the head temperature was 22° C. Heating was continued for ~5.5 hours. Final pot and head temperatures were 150° C. and 67° C. respectively. The weight of the distillate was 55 g.

Table 2 summarizes the analytical data for reaction products obtained in the experiments of Examples 1A and 1B. The principal monomer produced in both experiments was Me$_2$SiCl$_2$. The gravimetric ratio of the other monomers to methyltrichlorosilane was 25.05 in Example 1A and 4.18 in Example 1B. The highly methylated disilanes, Me$_3$SiSiMe$_3$, Me$_3$SiSiMe$_2$Cl and ClMe$_2$SiSiMe$_2$Cl present in the starting material were all either fully converted or substantially converted to monomers. For example, 9.46 g (0.065 mole) Me$_3$SiSiMe$_3$ was present in the feed material in Example 1A, but the final reaction product contained 6.53 g (0.045 mole) of Me$_3$SiSiMe$_3$. Conversion was 31%.

TABLE 2

COMPOSITION OF THE REACTION PRODUCTS FROM EXAMPLES 1A-1B

| STARTING MATERIAL | | | EXAM- | EXAM- |
|---|---|---|---|---|
| COMPOUND | Wt % | PRODUCT | PLE 1A | PLE 1B |
| | | Me$_2$SiHCl, wt % | 3.75 | 2.72 |
| MeSiCl$_3$ | 5.01 | MeSiHCl$_2$, wt % | 4.28 | 11.89 |
| Me$_2$SiCl$_2$ | 12.64 | Me$_3$SiCl, wt % | 9.18 | 6.81 |
| Me$_3$SiSiMe$_3$ | 9.46 | MeSiCl$_3$, wt % | 2.94 | 17.53 |
| Me$_3$SiSiMe$_2$Cl | 19.50 | Me$_2$SiCl$_2$, wt % | 56.44 | 52.64 |
| ClMe$_2$SiSiMe$_2$Cl | 24.43 | Me$_3$SiSiMe$_3$, wt % | 6.20 | 5.03 |
| Cl$_2$MeSiSiMe$_2$Cl | 5.05 | Me$_3$SiSiMe$_2$Cl, wt % | 3.98 | |
| Cl$_2$MeSiSiMeCl$_2$ | 23.91 | Higher Boilers | 13.25 | 3.38 |

Likewise in Example 1A, 83 percent of the ClMe$_2$SiSiMe$_2$Cl and all of the Cl$_2$MeSiSiMe$_2$Cl and Cl$_2$MeSiSiMeCl$_2$ were converted. Thus, both at atmospheric and autogenous pressures, the mixed 2-methylimidazole/tetrabutylphosphonium chloride catalyst afforded the cleavage of both the conventionally cleavable and uncleavable methylchlorodisilanes to produce a highly valued monomer composition.

Example 2

This example illustrates cleavage of (ClMe$_2$Si)$_2$, Me$_3$SiSiMe$_2$Cl and carbosilanes (disilamethanes) contained in the reaction residue from conventional hydrochlorination of the disilane fraction boiling at 140-170° C.

The experiment was conducted with 20 g residue derived from the hydrochlorination of the disilane fraction, 1 g 2-methylimidazole (99% purity, Aldrich) and 1 g (n-C$_4$H$_9$)$_4$PCl (96% purity, Aldrich) using the procedure described in Example 1A, except that no CH$_3$Cl was used. There was still tributylamine/tributylamine hydrochloride in the residue used as feedstock. With the stirrer set to 154 rpm, the autoclave was heated to 175° C. and maintained between 175-179° C. for one hour. Maximum autogenous pressure was 386 kPa (56 psig); residual pressure on cooling to room temperature was 124.1 kPa (18 psig). 17.2 g liquid was withdrawn for characterization. Table 3 shows the composition of the starting material and reaction mixture as determined by gas chromatography.

TABLE 3

COMPOSITION OF STARTING MATERIAL AND PRODUCT MIXTURE FOR EXAMPLE 2

| STARTING MATERIAL | Wt % | PRODUCT | Wt % |
|---|---|---|---|
| MeSiHCl$_2$ | 1.23 | Me$_2$SiHCl | 8.49 |
| Me$_3$SiCl | 0.37 | MeSiHCl$_2$ | 0.00 |
| MeSiCl$_3$ | 16.28 | Me$_3$SiCl | 1.91 |
| Me$_2$SiCl$_2$ | 19.03 | MeSiCl$_3$ | 3.27 |
| Me$_3$SiSiMe$_3$ | 2.32 | Me$_2$SiCl$_2$ | 26.36 |
| Me$_3$SiSiMe$_2$Cl | 0.69 | Me$_3$SiSiMe$_3$ | 2.02 |
| ClMe$_2$SiSiMe$_2$Cl | 40.10 | Me$_3$SiSiMe$_2$Cl | 1.92 |
| ClMe$_2$SiSiMeCl$_2$ | 3.82 | ClMe$_2$SiSiMe$_2$Cl | 12.88 |
| Higher Boilers* | 16.17 | ClMe$_2$SiSiMeCl$_2$ | 7.41 |
| | | Higher Boilers* | 35.74 |

*Higher Boilers = (Carbosilanes + Siloxanes + Polysilanes)

The data show that additional methylchlorosilane monomers were obtainable from what would normally be the waste from the conventional hydrochlorination cleavage process. There were 8.02 g (0.043 mole) ClMe$_2$SiSiMe$_2$Cl in the feed and 2.21 g (0.012 mole) in the reaction product. The feed contained 3.26 g (0.022 mole) MeSiCl$_3$ and 3.81 g (0.029 mole) Me$_2$SiCl$_2$. The reaction product contained 0.56 g (0.004 mole) MeSiCl$_3$ and 4.53 g (0.035 mole) Me$_2$SiCl$_2$.

Thus, conversion of the ClMe$_2$SiSiMe$_2$Cl contained in the starting material was 72% and conversion of MeSiCl$_3$ was ~82%. Methylchlorosilane monomers comprised 40 weight percent of the liquid product. The valuable monomers, Me$_2$SiHCl and Me$_2$SiCl$_2$, accounted for 87 weight percent of the monomer fraction. The gravimetric ratio of all other monomers to methyltrichlorosilane was 11.24.

Example 3

This example illustrates the cleavage of a sample of ClMe$_2$SiSiMe$_2$Cl with a catalyst containing equal weights of 2-methylimidazole and tetra(n-butyl)phosphonium chloride. The molar ratio of 2-methylimidazole to tetra(n-butyl)phosphonium chloride was 3.59.

The experiment was conducted in a 300 ml autoclave using the procedure described in Example 1A. 20 g ClMe$_2$SiSiMe$_2$Cl (95% purity, Gelest, Inc.), 1 g tetra(n-butyl)phosphonium chloride (96% purity, Aldrich) and 1 g 2-methyl-imidazole (99% purity, Aldrich) were charged to the autoclave. Reaction was done at 172-177° C. for 1 hour. Maximum autogenous pressure was 585.99 kPa (85 psig). On cooling the reactor to room temperature, the residual pressure of 122.02 kPa (17.7 psig) was discharged slowly. 19.9 g liquid reaction mixture was recovered for characterization by GC, GC/MS and $^{29}$Si NMR.

Compounds identified by GC/MS were Me$_2$SiHCl, Me$_3$SiCl, Me$_2$SiCl$_2$, (ClMe$_2$Si)$_2$, Me$_2$Si(SiMe$_2$Cl)$_2$, (ClMe$_2$Si—SiMe$_2$)$_2$ and Me$_2$Si(Me$_2$Si—SiMe$_2$Cl)$_2$. Table 4 summarizes the quantitative $^{29}$Si NMR analysis of the starting material and GC analysis of the reaction product. The data show 87.8 mole % conversion of ClMe$_2$SiSiMe$_2$Cl with the catalyst and reaction conditions used in the experiment.

As a comparison, Herzog et al. reported that when ClMe$_2$SiSiMe$_2$Cl was heated in the presence of N-methylimidazole under reflux conditions, a solid compound, identified as the addition complex of Me$_2$SiCl$_2$ and N-methylimidazole, and the polysilanes Me$_2$Si(SiMe$_2$Cl)$_2$, (ClMe$_2$Si—

SiMe$_2$)$_2$ and Me$_2$Si(Me$_2$Si—SiMe$_2$Cl)$_2$ were the principal reaction products. See Herzog, et al, *J. Organometallic Chemistry*, vol 507 (1996) 221-228

TABLE 4

COMPOSITION OF STARTING MATERIAL AND PRODUCT MIXTURE FOR EXAMPLE 3

| STARTING MATERIAL | Mole % | PRODUCT | wt % |
|---|---|---|---|
| Me$_3$SiSiMe$_2$Cl | 2.28 | Me$_2$SiHCl | 14.22 |
| Me$_3$SiSiMeCl$_2$ | 2.37 | Me$_3$SiCl | 4.23 |
| ClMe$_2$SiSiMe$_2$Cl | 95.35 | Me$_2$SiCl$_2$ | 56.54 |
|  |  | ClMe$_2$SiSiMe$_2$Cl | 9.41 |
|  |  | Polysilanes | 15.61 |

Example 4

This Example shows that the catalysts of this invention can catalyze the reaction of MeSiCl$_3$ and ClMe$_2$SiSiMe$_2$Cl to produce a methylchlorosilane monomer composition rich in the commercially valuable monomers, Me$_2$SiCl$_2$, Me$_2$SiHCl, Me$_3$SiCl and MeSiHCl$_2$.

Reaction was performed in the 300 ml PARR autoclave described in Example 1A. 9 g (0.06 mole) of MeSiCl$_3$ and 11 g (0.06 mole) of ClMe$_2$SiSiMe$_2$Cl (95% purity, Gelest) were placed in the reactor along with 1.5 g of tetra(n-butyl)phosphonium chloride (96% purity, Aldrich) and 0.5 g of 2-methylimidazole (99% purity, Aldrich). The molar ratio of 2-methylimidazole to tetra(n-butyl)phosphonium chloride was 1.20. The reactor was sealed and the reaction mixture was stirred (155 rpm) and heated to 265° C. This temperature was maintained for 3 hr. Maximum pressure was 1723.5 kPa (250 psig). Thereafter, the reactor was cooled to room temperature. Residual pressure was 186.1 kPa (27 psig).

GC analysis of the liquid reaction product showed that MeSiCl$_3$ and ClMe$_2$SiSiMe$_2$Cl had been converted to monomers, mainly Me$_2$SiCl$_2$, as shown in table 5 below. MeSiCl$_3$ was 45 wt % of the starting material, but only about 4 wt % of the reaction product. ClMe$_2$SiSiMe$_2$Cl decreased from 55 wt % of the starting material to about 2 wt % (included in Higher Boilers in Table 5) in the product. This result suggests that redistribution had occurred between MeSiCl$_3$ and ClMe$_2$SiSiMe$_2$Cl and that cleavage of the resulting Cl$_2$MeSiSiMe$_2$Cl to monomers had also occurred. Thus, the catalytic process of the instant invention gives a different result from that disclosed in U.S. Pat. No. 4,393,229, wherein AlCl$_3$ is the catalyst and a hydrosilane is a promoter.

TABLE 5

COMPOSITION OF REACTION PRODUCT OF EXAMPLE 4

| Me$_2$SiHCl, wt % | MeSiHCl$_2$, wt % | Me$_3$SiCl, wt % | MeSiCl$_3$, wt % | Me$_2$SiCl$_2$, wt % | Higher Boilers, wt % |
|---|---|---|---|---|---|
| 2.60 | 8.93 | 3.26 | 4.11 | 74.07 | 7.02 |

Example 5A-5B

This Example illustrates cleavage of the Direct Process Residue used in Example 1 with the catalysts: (tri(n-hexyl) tetradecylphosphonium chloride+1,2,4-triazole) and (tri(n-butyl)tetradecylphosphonium chloride+4-methyl-imidazole). Reactions were done in glassware at atmospheric pressure as described in Example 1B.

Example 5A 2 g (Tri(n-hexyl)tetradecylphosphonium chloride) (CYPHOS® IL 101) and 3 g 1,2,4-triazole (98.5% purity, Aldrich) were first stirred and heated together in the flask, which was purged with a slow nitrogen flow. The molar ratio of triazole to phosphonium chloride was 11.28. The solid triazole became fully soluble in the liquid phosphonium chloride by 60° C. Heating was discontinued and the flask cooled back to room temperature. 52 g uncleavable disilane residue having the composition shown in Table 2 was then added to the flask and the mixture was stirred and heated to a set temperature of 180° C. Distillation began when the flask temperature was 118° C. and the head temperature read 75° C. 32 g distillate was collected over the next hour. Maximum flask and head temperatures were 176.5° C. and 129° C., respectively.

Material retained in the flask solidified to a wax after the flask had cooled below 30° C. Another 53 g of the disilane residue was added to the flask and heating and stirring were ecommenced. 46.1 g distillate was collected during the ensuing hour. Maximum flask and head temperatures were 175° C. and 105° C., respectively. The temperature was allowed to cool to 23° C. The material left in the flask was a dark brown liquid. It weighed 22.4 g.

Example 5B

An experiment similar to that of Example 5A was performed with 1 g of 4-methyl-imidazole, 1.5 g of tri(n-butyl) tetradecylphosphonium chloride (CYPHOS® 3453) and 50 g of the uncleavable disilane residue used in Example 1. The molar ratio of 4-methylimidazole to tri(n-butyl)tetradecylphosphonium chloride was 3.45. Heat and stirring were applied as in Example 5A. 38.4 g distillate was collected in the course of an hour. The flask temperature reached 175° C. and the head temperature 136° C.

Another 50 g uncleavable disilane residue was added to what was retained in the cooled reaction flask and heating and stirring repeated as described above. The weight of the distillate was 42 g and that of the residual dark brown liquid, was 17.2 g.

Table 6 summarizes the higher boilers conversion as well as the quantitative analysis of the monomer portion of the four distillates collected in the experiments of Examples 5A and 5B. Monomer yield represents the portion of the distillate product attributable to the methylchlorosilane monomers as determined by gas chromatography.

The results show that mixtures of tri(n-hexyl)tetradecylphosphonium chloride and 1,2,4-triazole as well as mixtures of 4-methylimidazole and tri(n-butyl)tetra-decylphosphonium chloride are effective at catalyzing the formation of methylchlorosilane monomers from conventionally uncleavable Direct Process residue. The data for both sets of experiments also show that each charge of conventionally uncleavable residue was converted to methylchlorosilane monomers. Thus, the catalysts were reusable. Overall catalyst loading was halved from 10 wt % to 5 wt %. The concentrations of Me$_2$SiCl$_2$ and MeSiHCl$_2$ in distillate changed significantly from the first to the second charge. The large increases in Me$_2$SiCl$_2$ (D) and small decreases in MeSiCl$_3$ (T) contributed to the beneficial changes in the T/D ratio.

TABLE 6

SUMMARY OF ANALYTICAL DATA FOR
METHYLCHLOROSILANE MONOMER FRACTION OF
THE DISTILLATES IN EXAMPLES 5A & 5B

|  | EXAMPLE 5A | | EXAMPLE 5B | |
| --- | --- | --- | --- | --- |
|  | First Distillate | Second Distillate | First Distillate | Second Distillate |
| Monomer Yield, % | 36.55 | 46.64 | 40.47 | 43.52 |
| $Me_2SiHCl$, wt % | 0.25 | 2.23 | 1.30 | 1.09 |
| $MeSiHCl_2$, wt % | 23.28 | 5.06 | 9.02 | 3.57 |
| $Me_3SiCl$, wt % | 2.89 | 3.71 | 3.33 | 4.98 |
| $MeSiCl_3$, wt % | 35.32 | 33.11 | 36.61 | 33.54 |
| $Me_2SiCl_2$, wt % | 38.26 | 55.88 | 49.53 | 56.82 |
| T/D | 0.92 | 0.59 | 0.74 | 0.59 |

Example 6A-6F

This example illustrates the reusability of the catalyst, 2-methylimidazole plus tetra(n-butyl)phosphonium chloride, in the cleavage of conventionally uncleavable Direct Process residue.

The residue used was that already described in Examples 1, 5A and 5B. The catalyst was made with 2.5 g 2-methylimidazole (98.5% purity) and 2.5 g CYPHOS® 443 (tetra(n-butyl)phosphonium chloride). The experimental procedure was that described in Examples 5A and 5B, except that a total of six residue batches were reacted on this single catalyst charge. The weight of each batch, along with that of the recovered distillate, is shown in Table 7 below.

The results show that catalysis was sustained through at least six batches. A total of 308.73 g residue was charged. Overall, catalyst usage was decreased from the initial 10 wt % to 1.6 wt %. As in Examples 5A and 5B, $MeSiHCl_2$ was higher in the first distillate than in subsequent ones. $Me_2SiCl_2$ (D), $MeSiCl_3$ (T) and T/D remained acceptably stable in Examples 6B through 6F.

TABLE 7

COMPOSITION OF MONOMERS FRACTION FROM THE
EXPERIMENTS OF EXAMPLES 6A-6F

|  | EX 6A | EX 6B | EX 6C | EX 6D | EX 6E | EX 6F |
| --- | --- | --- | --- | --- | --- | --- |
| Weight Charged, g | 50.00 | 50.00 | 49.00 | 52.93 | 52.80 | 54.00 |
| Distillate, g | 38.00 | 40.40 | 40.20 | 38.00 | 43.20 | 47.00 |
| Monomer Yield, % | 45.67 | 44.61 | 46.17 | 40.83 | 42.52 | 44.13 |
| $Me_2SiHCl$, wt % | 1.51 | 1.59 | 1.56 | 1.03 | 0.62 | 0.95 |
| $MeSiHCl_2$, wt % | 14.43 | 4.65 | 4.80 | 4.99 | 4.64 | 4.40 |
| $Me_3SiCl$, wt % | 3.73 | 6.17 | 5.68 | 4.42 | 3.75 | 3.61 |
| $MeSiCl_3$, wt % | 24.33 | 26.68 | 27.27 | 27.33 | 29.83 | 29.75 |
| $Me_2SiCl_2$, wt % | 56.00 | 60.91 | 60.69 | 62.23 | 61.17 | 61.29 |
| T/D | 0.43 | 0.44 | 0.45 | 0.44 | 0.49 | 0.49 |

Comparative Examples 7A, 7B and Example 7C

These Examples illustrate the synergy in formation of $Me_2SiHCl$ from the uncleavable hydrochlorination residue when the catalyst comprises mixtures of onium salts and heterocyclic amines The three experiments of this Example were done in glassware at atmospheric pressure and 85-185° C., as described in Example 1B, with uncleavable hydrochlorination residue and either 2-methylimidazole (98.5% purity, BASF), tetra(n-butyl)phosphonium chloride (CYPHOS® 443) or a 1:1 mixture of the two.

GC/MS analysis of uncleavable hydrochlorination residue permitted identification of its principal components (see Table 8). $MeSiCl_3$ and $Me_2SiCl_2$ were the only monomers present. Together, they were 8.43 area % of the peaks. The T/D ratio was 1.39. Higher boilers were 91.57 area % of the peaks in the chromatogram. Of these, methylchlorodisilanes were collectively 26.64 area %, carbosilanes 57.66 area % and siloxanes and polysilanes together were 7.27 area %.

TABLE 8

COMPOUNDS IN UNCLEAVABLE HYDROCHLORINATION
RESIDUE IDENTIFIED BY GC/MS

| NUMBER | COMPOUND |
| --- | --- |
| 1 | $MeSiCl_3$ and $Me_2SiCl_2$ |
| 2 | $Me_3SiSiMe_3$ |
| 3 | $Me_3SiSiMe_2Cl$ |
| 4 | $Me_3Si-CH_2-SiMe_3$ |
| 5 | $ClMe_2SiOSiMe_2Cl$ |
| 6 | $Cl_2MeSiOSiMe_2Cl$ |
| 7 | $ClMe_2SiSiMe_2Cl$ |
| 8 | $Me_3Si-CH_2-SiMe_2Cl$ |
| 9 | $ClMe_2Si-CH_2-SiMe_2Cl$ |
| 10 | $Me_3Si-CH_2-SiMeCl_2$ |
| 11 | $ClMe_2Si-CH_2-SiMeCl_2$ |
| 12 | $Cl_2MeSi-CH_2-SiMeCl_2$ |
| 13 | $Cl_3Si-CH_2-SiMeCl_2$ |
| 14 | $Me_2Si(SiMe_2Cl)_2$ |
| 15 | $Me_3Si(SiMe_2)SiMe_2Cl$ |
| 16 | $Cl_2MeSi-(SiMeCl)-SiMeCl_2$ |
| 17 | $(C_4H_9)_3N$ |

Quantitative GC analysis of the reaction products is summarized in Table 9. The data show that the (2-Methylimidazole+$Bu_4PCl$) catalyst yielded a product that had more than twice the amount of $Me_2SiHCl$ as either individual compound did. $MeSiHCl_2$ formation was also enhanced. Overall, the gravimetric ratio of the other methylchlorosilanes to methyltrichlorosilane was 3.71, which was higher than the 3.09 with $Bu_4PCl$ and 2.06 with 2-methyl-imidazole. Thus, (2-Methylimidazole+$Bu_4PCl$) enhanced the formation of the more valuable methylchlorosilanes from the uncleavable hydrochlorination residue. Moreover, the cleavage reactions occurred in the presence of tributylamine/tributylamine hydrochloride without any apparent inhibition.

TABLE 9

COMPOSITION OF REACTION PRODUCTS
FOR THE COMPARATIVE EXAMPLES
7A, 7B AND EXAMPLE 7C

| COMPOUND | COMP EXP 7A 50 g Residue + 2-Methyl-imidazole, 5 g | COMP EXP 7B 50 g Residue + $BU_4PCl$, 5 g | EXP 7C 100 g Residue + 2-Methyl-imidazole, 5 g + $Bu_4PCl$, 5 g |
| --- | --- | --- | --- |
| $(CH_3)_2SiHCl$, wt % | 6.42 | 6.72 | 15.37 |
| $CH_3SiHCl_2$, wt % | 7.63 | 6.92 | 9.34 |
| $(CH_3)_3SiCl$, wt % | 5.82 | 9.43 | 9.38 |
| $CH_3SiCl_3$, wt % | 27.34 | 23.30 | 20.29 |
| $(CH_3)_2SiCl_2$, wt % | 36.42 | 48.98 | 41.21 |
| Higher Boilers, wt % | 16.38 | 4.64 | 4.41 |
| Yield, g | 6.5 | 24.3 | 40 |
| T/D | 0.75 | 0.48 | 0.49 |

Examples 8A, 8B and Comparative Examples 8C to 8E

This Example illustrates the catalytic activity and reusability of (2-Methylimidazole+n-Bu$_4$PCl) compositions across a wide range of gravimetric ratios. Each of the Examples or Comparative Comparatives, 8A through 8D, was run at a different ratio of 2-methylimidazole to tetra(n-butyl)phosphonium chloride. However, the total weight of catalyst was always 5.0 g. Additionally, each experiment in Examples or Comparative Examples 8A through 8D consisted of four separate batch reactions of conventionally uncleavable residue (~50 g) with a single charge of catalyst. No catalyst was used with the single charge of Direct Process Residue in Example 8E. The reactions were done in glassware at atmospheric pressure with heating from room temperature to ~200° C., as described above in Example 6, using Direct Process residue containing 10.25 wt % CH$_3$SiCl$_3$ (T), 9.24 wt % (CH$_3$)$_2$SiCl$_2$ (D) and 80.51 wt % conventionally uncleavable compounds. The experimental data are summarized in Tables 10-13.

Example 8A was done with 4 g 2-Methylimidazole and 1 g n-Bu$_4$PCl. Example 8B was done with 1 g 2-Methylimidazole and 4 g n-Bu$_4$PCl. Comparative Example 8C used 5 g n-Bu$_4$PCl only and Comparative Example 8D 5 g 2-Methylimidazole Only. No catalyst was used in Comparative Example 8E.

In the tables, "Weight Percent" refers to the percentage by weight of the compound in the methylchlorosilane monomer fraction from all four batch experiments. "Total Weight" is the cumulative weight of the compound from all four batch experiments. "Net Weight" is the difference between the total weight and the cumulative weight of each compound present in the overall weight of Direct Process Residue charged to the four batch experiments.

TABLE 10

SUMMARY OF CALCULATED VALUES FOR EXAMPLE 8A (4 Batches charged on 4 g 2-Methylimidazole + 1 g Bu$_4$PCl)

|  | (CH$_3$)$_2$SiHCl | CH$_3$SiHCl$_2$ | (CH$_3$)$_3$SiCl | CH$_3$SiCl$_3$ | (CH$_3$)$_2$SiCl$_2$ |
|---|---|---|---|---|---|
| Weight Percent | 8.42 | 14.11 | 3.50 | 17.02 | 56.94 |
| Total Weight, g | 5.16 | 8.65 | 2.15 | 10.43 | 34.87 |
| Net Formation, g | 5.16 | 8.65 | 2.15 | (−10.33) | 16.16 |

Total charge for 4 batches = 202.50 g. Total distillate = 90.90 g. Weight of methylchlorosilane monomers = 61.25 g.

TABLE 11

SUMMARY OF CALCULATED VALUES FOR EXAMPLE 8B (4 Batches charged on 1 g 2-Methylimidazole + 4 g Bi$_4$PCl)

|  | (CH$_3$)$_2$SiHCl | CH$_3$SiHCl$_2$ | (CH$_3$)$_3$SiCl | CH$_3$SiCl$_3$ | (CH$_3$)$_2$SiCl$_2$ |
|---|---|---|---|---|---|
| Weight Percent | 8.43 | 11.23 | 3.23 | 14.99 | 62.12 |
| Total Weight, g | 5.22 | 6.95 | 2.00 | 9.28 | 38.46 |
| Net Formation, g | 5.22 | 6.95 | 2.00 | (−11.43) | 19.79 |

Total charge for 4 batches = 202.10 g. Total distillate = 82.90 g. Weight of methylchlorosilane monomers = 61.92 g

TABLE 12

SUMMARY OF CALCULATED VALUES FOR COMPARATIVE EXAMPLE 8C (4 Batches charged on 5 g Bu$_4$PCl)

|  | (CH$_3$)$_2$SiHCl | CH$_3$SiHCl$_2$ | (CH$_3$)$_3$SiCl | CH$_3$SiCl$_3$ | (CH$_3$)$_2$SiCl$_2$ |
|---|---|---|---|---|---|
| Weight Percent | 2.17 | 12.91 | 2.46 | 34.79 | 47.65 |
| Total Weight, g | 0.93 | 5.51 | 1.05 | 14.83 | 20.32 |
| Net Formation, g | 0.93 | 5.51 | 1.05 | (−5.85) | 1.67 |

Total charge for 4 batches = 201.80 g. Total distillate = 94.02 g. Weight of methylchlorosilane monomers = 42.63 g

TABLE 13

SUMMARY OF CALCULATED VALUES FOR COMPARATIVE EXAMPLE 8D (4 Batches charged on 5 g 2-Methylimidazole)

|  | (CH$_3$)$_2$SiHCl | CH$_3$SiHCl$_2$ | (CH$_3$)$_3$SiCl | CH$_3$SiCl$_3$ | (CH$_3$)$_2$SiCl$_2$ |
|---|---|---|---|---|---|
| Weight Percent | 9.90 | 11.76 | 2.63 | 25.18 | 50.53 |
| Total Weight, g | 4.75 | 5.64 | 1.26 | 12.08 | 24.24 |
| Net Formation, g | 4.75 | 5.64 | 1.26 | (−8.73) | 5.48 |

Total charge for 4 batches = 203.0 g. Total distillate = 73.20 g. Weight of methylchlorosilane monomers = 48.01 g

TABLE 14

SUMMARY OF CALCULATED VALUES FOR COMPARATIVE
EXAMPLE 8E (1 Batch charged with no catalyst)

|  | $(CH_3)_2SiHCl$ | $CH_3SiHCl_2$ | $(CH_3)_3SiCl$ | $CH_3SiCl_3$ | $(CH_3)_2SiCl_2$ |
|---|---|---|---|---|---|
| Weight Percent | 1.16 | 18.62 | 1.12 | 37.11 | 41.99 |
| Total Weight, g | 0.07 | 1.10 | 0.06 | 2.19 | 2.48 |

Total charge = 54.2 g. Total distillate = 5.90 g. Weight of methylchlorosilane monomers = 4.56 g The effective catalyst usage for the four batch experiments of Examples 8A and 8B was 2.5 weight percent.

The results show that simply heating 54.2 g conventionally uncleavable residue in the absence of a catalyst (Comparative Example 8E) yielded only 4.56 g methylchlorosilane monomers (8.41% based on the charge), with a T/D ratio 0.88. When 2-methylimidazole was used as catalyst (Comparative Example 8D), the yield of methylchloro-silane monomers per batch was 12.00 g and the T/D ratio in the reaction product was 0.50. With n-Bu$_4$PCl (Comparative Example 8C), monomer yield per batch was 10.66 g and T/D ratio 0.73. Monomer yield per batch increased when mixtures of 2-methylimidazole and n-Bu$_4$PCl were used as catalysts (Examples 8A and 8B). In Example 8A, with a 4:1 gravimetric ratio of 2-methylimidazole to n-Bu$_4$PCl, the yield per batch was 15.31 g and the T/D ratio 0.30. In Example 8B, with a 1:4 gravimetric ratio of 2-methylimidazole to n-Bu$_4$PCl, monomer yield per batch was 15.48 g and T/D ratio 0.24. Additionally, formation of the highly valuable monomers (($CH_3)_2SiHCl$, $CH_3SiHCl_2$, $(CH_3)_3SiCl$) was enhanced with the use of mixtures of 2-methylimidazole and n-Bu$_4$PCl. In summary, the experiments of these examples illustrate catalyst reusability as well as the increased conversion of compounds in the conventionally uncleavable residue, increased monomer yield, lower T/D ratios, and production of commercially more valuable monomers when mixtures of 2-methylimidazole and n-Bu$_4$PCl were used as the catalyst for the cleavage of Direct Process Residue.

Example 9

This Example illustrates combinations of tetraalkylphosphonium halides and heterocyclic amines wherein the combinations are liquid at temperatures below 100° C.

Two methods were employed. In Method A, The experiments were performed by adding a weighed amount of solid tetraalkylphosphonium halide to a test tube followed by heating in an oil bath. A record was made both of the temperature at which liquid was first observed and that at which the mass became completely liquid. The heterocyclic amine was then added; and the mixture was stirred to obtain full dissolution. The mixture was then allowed to cool; and the temperature of solid formation (if any) was noted.

Method B was used with some solid tetraalkylphosphonium halides and with those that were already liquid at room temperature (20-25° C.). In this case, weighed quantities of tetraalkylphosphonium halide and heterocyclic amine were added to the test tube; and the mixtures was heated (if necessary) to observe their solubility behavior. The 1:1 mixture prepared in Example 9I was subjected to DSC thermal analysis along with the individual starting materials.

TABLE 14

OBSERVATIONS ON THE MELTING BEHAVIOR OF MIXTURES
OF IMIDAZOLES AND PHOSPHONIUM CHLORIDES

| EXAMPLE | MATERIALS USED | METHOD | OBSERVATIONS |
|---|---|---|---|
| 9A | CYPHOS ® 443, 2 g and 2-Methylimidazole, 2 g | A | CYPHOS ® 443 began melting ~57° C. Melting complete by 70° C. 2-Methylimidazole was fully dissolved by 75-78° C. Solid on cooling below ~45° C. |
| 9B | CYPHOS ® 443, 2 g and 2-Isopropylimidazole, 2 g | A | CYPHOS ® 443 began melting ~57° C. Melting complete by 70° C. 2-Isopropylimidazole was fully dissolved by 81-85° C. Clear viscous liquid on cooling to room temperature |
| 9C | CYPHOS ® 443, 2 g and 4-Methylimidazole, 2 g | B | Liquid observed ~57° C. Clear, homogeneous liquid 65-67° C. No soild. Clear free flowing liquid at room temperature |
| 9D | CYPHOS ® 3453, 3 g and 2-Methylimidazole, 3 g | B | Liquid observed ~45° C. Complete dissolution by 105-108° C. Solid on cooling below ~ 40° C. |
| 9E | CYPHOS ® 3453, 3 g and 1-Methylimidazole, 3 g | B | Liquid observed ~45° C. Clear homogeneous liquid by 78° C. Solid on cooling below ~40° C. |
| 9F | CYPHOS ® IL 101, 4 g and 1-Methylimidazole, 4 g | B | 1-Methylimidazole was fully dissolved by 75° C. Both solid and liquid observed on cooling to room temperature |
| 9G | CYPHOS ® IL 101, 5.4 g and 2-Methylimidazole, 5.4 g | B | 2-Methylimidazole was fully dissolved by 120° C. Only solid observed on cooling to room temperature |

TABLE 14-continued

OBSERVATIONS ON THE MELTING BEHAVIOR OF MIXTURES
OF IMIDAZOLES AND PHOSPHONIUM CHLORIDES

| EXAMPLE | MATERIALS USED | METHOD | OBSERVATIONS |
|---|---|---|---|
| 9H | CYPHOS ® IL 101, 5 g and 2-Ethylimidazole, 5 g | B | 2-Ethylimidazole was fully dissolved by 65° C. Only solid observed on cooling to room temperature |
| 9I | (n-$C_4H_9$)$_4$PCl (Aldrich) 5 g and 2-Methylimidazole (BASF, 99% purity), 5 g | B | DSC thermal analysis showed a sharp, intense melting endotherm at 145.85° C. for 2-methyl-imidazole and weaker, broad peak at 94.10° C., probably due to imidazole. (n-$C_4H_9$)$_4$PCl showed a broad melting event at 56.69° C. The mixed composition had a peak at 92.17° C. and a broad endotherm 100-140° C. No distinct 2-methylimidazole melting event. |

Comparative Examples 10A, 10B and Examples 10C, 10D

These Examples illustrate the enhanced residue cleavage obtained with combinations of heterocyclic ammonium chloride and quaternary Group 15 onium compounds, wherein both the heterocyclic ammonium chloride and the quaternary Group 15 onium compound are ionic liquids. The heterocyclic ammonium chloride used was 1-methylimidazolium chloride (melting point 75° C.) and the quaternary Group 15 onium compounds were tetra(n-butyl)phosphonium chloride (melting point 57° C.) and (tri n-hexyl)tetradecylphosphonium chloride (melting point<0° C.). Conventionally uncleavable Direct Process Residue, described already in Example 7, was the feed material.

Each of the four experiments (Comparative Examples 10A, 10B and Examples 10C, 10D) was run in glassware, with ~50 g feed, as described hereinabove in Example 1B. No catalyst was used in Comparative Example 10A, but 5 g catalyst was added to the feed in each of the other three examples. Comparative Example 10B is a control done with 5 g 1-methyl-imidazolium chloride (1-MIMCl). Example 10C had 2.5 g each of 1-methyl-imidazolium chloride (1-MIMCl) and (tri n-hexyl)tetradecylphosphonium chloride (CYPHOS® IL 101). Example 10D was run with 2.5 g each 1-methylimidazolium chloride and tetra(n-butyl)phosphonium chloride (CYPHOS® 443).

Gas chromatographic analysis of the distillates is summarized in Table 15.

TABLE 15

SUMMARY OF EXPERIMENTAL DATA FOR COMPARATIVE
EXAMPLES 10A, 10B AND EXAMPLES 10C, 10D

|  | COMPARATIVE EXAMPLE 10A | COMPARATIVE EXAMPLE 10B | EXAMPLE 10C | EXAMPLE 10D |
|---|---|---|---|---|
| Catalyst | None | 1-MIMCl, 5 g | 1-MIMCl, 2.5 g + CYPHOS ® IL 101, 2.5 g | 1-MIMCl, 2.5 g + CYPHOS ® 443, 2.5 g |
| Direct Process Residue, g | 54.2 | 52.0 | 53.0 | 53.0 |
| Weight of Distillate, g | 30.2 | 26.5 | 19.0 | 20.0 |
| Weight of Residue in Flask, g | 27.5 | 28.3 | 38.3 | 37.0 |
| Monomers Formed | T, D | MH, M, T, D | M2H, MH, M, T, D | M2H, MH, M, T, D |
| Monomers Area % | 20.26 | 19.31 | 48.51 | 42.45 |
| T/D Ratio | 1.34 | 1.27 | 1.05 | 1.13 |
| Higher Boilers Area % | 79.74 | 80.69 | 51.49 | 57.55 |

M2H = $Me_2SiHCl$, MH = $MeSiHCl_2$, M = $Me_3SiCl$, T = $MeSiCl_3$, D = $Me_2SiCl_2$

The data show that in the absence of added catalyst, the composition of the distillate was similar to that of the conventionally uncleavable Direct Process Residue used as the feed material. T/D ratio was 1.39 in the latter and 1.34 in the distillate of Comparative Example 10A. $MeSiCl_3$ and $Me_2SiCl_2$ were the only monomers in the distillate and the monomer yield was 11.3% based on the weight of residue charged. When 1-methylimidazolium chloride was the catalyst (1-MIMCl, Comparative Example 10B), small amounts of MH and M were in the distillate along with major components, T and D. Monomer yield was 9.9% and the T/D ratio was 1.27.

Significant improvements in monomer yield and T/D ratio were observed in Examples 10C and 10D, wherein the catalysts comprised a heterocyclic ammonium chloride that is an ionic liquid and a quaternary phosphonium chloride that is also an ionic liquid. The combination of 1-methylimidazolium chloride and CYPHOS® IL 101 in Example 10C afforded a 17.4% monomer yield and a T/D ratio of 1.05, which was lower than the ratios in the comparative examples 10A and 10B. Small amounts of M2H and MH were present along with the major monomers, M, T and D. Example 10D, with the combination of 1-methylimidazolium chloride and CYPHOS® 443 as the catalyst, produced similar results. Monomer yield was 16%, T/D ratio was 1.13 and M2H, MH, M, T, and D were all present in the distillate.

Example 11

This Example illustrates redistribution of $MeSiCl_3$ and $ClMe_2SiSiMe_2Cl$ in an ionic liquid catalyst comprising 1-methylimidazolium chloride and CYPHOS® IL 101 (tri(n-hexyl)tetradecylphosphonium chloride) to produce a methylchlorosilane monomer composition containing $Me_2SiCl_2$ and $Me_3SiCl$.

The experiment was conducted in glassware using the arrangement described in Example 1B. The only differences were use of a 100 ml round bottom flask and provision for attaching a syringe to deliver the mixture of $ClMe_2SiSiMe_2Cl$ (11 g, 0.06 mol) and $MeSiCl_3$ (9 g, 0.06 mol) into the ionic liquid catalyst. After the apparatus had been inerted with nitrogen flow, 25 g each of 1-methylimidazolium chloride and CYPHOS® IL 101 was added to the flask; and the stirred mixture was heated to 80° C. under a gentle flow of nitrogen. The mixture was completely liquid at that temperature. The temperature was raised to 175° C. before injection of $MeSiCl_3$ and $ClMe_2SiSiMe_2Cl$ commenced. The 20 g feed was injected over a 35 minute period; and the distillate was condensed continuously during the injection. A total of 6 g liquid was collected. GC analysis revealed that the composition contained: $Me_3SiCl$ (3.39 wt %), $MeSiCl_3$ (77.39 wt %) and $Me_2SiCl_2$ (19.22 wt %). Flashing of $MeSiCl_3$ without reaction was anticipated at a temperature that was more than double its normal boiling point. The results show that the distillate contained 4.64 g $CH_3SiCl_3$. Accordingly, $CH_3SiCl_3$ conversion was 48%. Of the 0.06 mole $CH_3SiCl_3$ added, 0.029 mole was converted. The product contained 0.009 mole $(CH_3)_2SiCl_2$ and the molar ratio of $(CH_3)_2SiCl_2$ to $(CH_3)_3SiCl$ was 4.77. Thus, methylchlorosilane monomer formation was realized from $MeSiCl_3$ and $ClMe_2SiSiMe_2Cl$ in a mixture of ionic liquids comprising a heterocyclic ammonium chloride and a Group 15 onium chloride.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

The invention claimed is:

1. A catalytic process for producing an organohalosilane monomer composition from a high-boiling residue, said process comprising
(A) heating the high-boiling residue in the presence of a catalyst comprising (1) one or more heterocyclic amines and/or one or more heterocyclic ammonium halides, and (2) one or more quaternary Group 15 onium compounds, optionally in the presence of an organohalide and/or a hydrogen halide and/or an inert gas,
at a temperature within the range of about 75° C. to about 300° C. under atmospheric pressure or superatmospheric pressure
to convert the high-boiling residue to an organohalosilane monomer composition containing at least one organohalosilane monomer having a general formula selected from the group consisting of $R^1SiHX_2$, $R^1{}_2SiHX$, $R^1{}_2SiX_2$ and $R^1{}_3SiX$, $R^1$ being an aromatic, aliphatic, alkaryl or cycloaliphatic univalent hydrocarbyl group, X being a halogen atom selected from the group consisting of fluorine, chlorine, bromine, and iodine, and
(B) optionally recovering the catalyst,
wherein the high-boiling residue comprises (1) an uncleavable component containing at least one of tetraorganodihalodisilanes and optionally one or more compounds selected from carbosilanes, organohalopolysilanes, hexaorganodisilanes, and pentaorganohalodisilanes; and (2) optionally a cleavable component containing at least one of diorganotetrahalodisilanes and triorganotrihalodisilanes with the proviso that if present, the cleavable component has a concentration less than that of the uncleavable component; and
wherein the quaternary Group 15 onium compound is of the general formula, $R_4Q^+X^-$, wherein each R is independently an alkyl, cycloalkyl, aryl or alkaryl group of from 1 to 30 carbon atoms, Q is phosphorus, arsenic, antimony and bismuth, and X is a halide selected from the group consisting of F, Cl, Br or I.

2. The process of claim 1 wherein the heterocyclic amine has at least one nitrogen atom in at least one 4- to 8-membered hydrocarbon ring, wherein the ring atoms adjacent to the nitrogen are carbon or nitrogen, and the hydrocarbon ring or rings are, independently of one another, aromatic or non-aromatic hydrocarbon rings.

3. The process of claim 2 wherein the heterocyclic amine has a pKa of about 6.9 to about 7.9.

4. The process of claim 2 wherein the heterocyclic amine contains a five-membered ring with 1 to 3 nitrogen atoms.

5. The process of claim 4 wherein the heterocyclic amine is selected from the group consisting of imidazole, 1-methylimidazole, 2-methylimidazole, 2-ethylimidazole, 2-isopropyl-imidazole, 4-methylimidazole, 2,4-dimethylimidazole, 2-(2-imidazolyl)imidazole, 2-phenylimidazole, imidazoline, imidazolidine, pyrazole, 3-methylpyrazole, pyrrolidone, N-methylpyrrolidone, 1,3-dimethyl-2-imidazolidone, 1,2,3-triazole, and 1,2,4-triazole.

6. The process of claim 1 wherein the heterocyclic ammonium halide is derived from a heterocyclic amine having at least one nitrogen atom in at least one 4- to 8-membered hydrocarbon ring, wherein the ring atoms adjacent to the nitrogen are independently carbon or nitrogen atoms, and the hydrocarbon ring or rings are, independently of one another, aromatic or non-aromatic hydrocarbon rings, wherein the halide is fluoride, chloride, bromide or iodide.

7. The process of claim 6 wherein the heterocyclic ammonium halide is derived from a heterocyclic amine with 1 to 3 nitrogen atoms in a five-membered ring, and the halide is fluoride, chloride, bromide or iodide.

8. The process of claim 7 wherein the heterocyclic ammonium halide is 1,2-dimethyl-3-(n-propyl)-imidazolium chloride, 1-ethyl-3-methylimidazolium bromide, 1,2-dimethyl-3-(n-butyl)imidazolium chloride, 1-butyl-3-methylimidazolium chloride, 1-(3-cyanopropyl)-3-methylimidazolium chloride, or 1-methylimidazolium chloride.

9. The process of claim 6 wherein the heterocyclic ammonium halide is an ionic liquid selected from the group consisting of 1-methylimidazolium chloride, 1-butyl-3-methylimidazolium chloride, and 1-(3-cyanopropyl)-3-methylimidazolium chloride.

10. The process of claim 1 wherein the quaternary Group 15 onium compound, $R_4Q^+X^-$, contains compounds of general formulae $R_3QHX$ and HX, wherein R is an alkyl, cycloalkyl, aryl or alkaryl group of from 1 to 30 carbon atoms, Q is phosphorus, antimony or arsenic, and X is F, Cl, Br or I.

11. The process of claim 1 wherein the quaternary Group 15 onium compound, $R_4Q^+X^-$, is tetra(n-butyl)phosphonium chloride, tetra(n-butyl)phosphonium bromide, trihexyl(tetradecyl)phosphonium bromide, methyltri(isobutyl)phosphonium bromide, methyltri(isobutyl)phosphonium chloride, tetra(n-octyl)phosphonium chloride, tri(n-butyl)tetradecylphosphonium chloride, or octyltri(butyl)phosphonium chloride.

12. The process of claim 11 wherein the quaternary Group 15 onium compound is an ionic liquid selected from the group consisting of tri(n-hexyl)tetradecylphosphonium chloride, tetra(n-butyl)phosphonium bromide, tetra(n-butyl)phosphonium chloride, tri(n-butyl)tetradecylphosphonium chloride, and methyltri(isobutyl)phosphonium chloride.

13. The process of claim 1 wherein the step (A) is conducted in the presence of an organohalide being methyl chloride or methyl bromide.

14. The process of claim 1 wherein the step (A) is conducted in the presence of a hydrogen halide being HCl or HBr.

15. The process of claim 1 wherein the step (A) is conducted in the presence of an inert gas being nitrogen or argon.

16. The process of claim 1 wherein $R^1$ is methyl, ethyl or phenyl and X is chloride or bromide.

17. The process of claim 1 wherein the organohalosilane monomer composition comprises $(CH_3)_2SiHCl$, $CH_3SiHCl_2$, $(CH_3)_3SiCl$, $(CH_3)_2SiCl_2$, and $CH_3SiCl_3$, wherein the content of $(CH_3)_2SiCl_2$ and $CH_3SiHCl_2$, individually or collectively, exceeds that of $CH_3SiCl_3$.

18. The process of claim 1 wherein the high-boiling residue is heated under a superatmospheric pressure of up to 7 MPa at 150° C. to 250° C. in a mechanically stirred reactor for a period of 30 to 120 minutes.

19. The process of claim 1 wherein the high-boiling residue is heated under ambient atmospheric pressure at 150° C. to 250° C.

20. The process of claim 1 wherein the catalyst contains 0.01 wt % to 99.95 wt % of (1) at least one or more heterocyclic amines and/or one or more heterocyclic ammonium halides, and 0.05 wt % to 99.9 wt % of (2) one or more quaternary Group 15 onium compound based on the total weight of components (1) and (2).

21. The process of claim 20 wherein the catalyst contains 5 wt % to 85 wt % of 2-methylimidazole and 95 wt % to 15 wt % of tetra(n-butyl)-phosphonium chloride based on the total weight of the 2-methylimidazole and the tetra(n-butyl)-phosphonium chloride.

22. The process of claim 21 wherein the molar ratio of 2-methylmidazole to tetra(n-butyl)phosphonium chloride is from 1.1 to 100.

23. The process of claim 21 wherein the 2-methylimidazole contains about 0.05 to about 5 weight percent of imidazole and the tetra(n-butyl)phosphonium chloride contains about 0.05 to about 5 weight percent of HCl and about 0.05 to about 5 weight percent of $(n-C_4H_9)_3PHCl$.

24. The process of claim 1 wherein the weight of the catalyst is 1 to 50 percent of the weight of the high-boiling residue.

25. The process of claim 1 wherein the catalyst is recovered and reused.

26. The process of claim 1 wherein multiple batches of the high-boiling residue are converted to the organohalosilane monomer composition on a single catalyst charge and the ultimate catalyst usage, defined as 100×(weight of the catalyst/total weight of the high-boiling residue), is about 0.1 to about 5 weight percent.

27. The process of claim 1 wherein the catalytic process comprises reactions selected from the group consisting of disproportionation, redistribution, silylene extrusion, silylene insertion and the combinations thereof.

28. The process of claim 27 wherein the reactions are conducted batchwise or continuously in ionic liquids in a mechanically-stirred reactor, a gas-sparged reactor or a bubble column.

* * * * *